United States Patent [19]

Peterson

[11] Patent Number: 5,396,812
[45] Date of Patent: Mar. 14, 1995

[54] SAMPLE SYSTEM

[76] Inventor: Roger Peterson, Rte. 1 box 316, Sweeny, Tex. 77480

[21] Appl. No.: 978,622

[22] Filed: Nov. 19, 1992

Related U.S. Application Data

[63] Continuation-in-part of Ser. No. 895,788, Jun. 9, 1992, Pat. No. 5,279,167, and Ser. No. 882,033, Jul. 13, 1992.

[51] Int. Cl.⁶ .................. G01N 01/10; G01N 01/14; G01N 01/22
[52] U.S. Cl. ............... 73/863.81; 73/863.25; 73/863.85; 73/864.14; 73/864.74
[58] Field of Search .......... 73/863.83, 863.86, 864.34, 73/864.74, 863.85, 863.25, 863.81, 23.42, 864.14

[56] References Cited

U.S. PATENT DOCUMENTS

| | | | |
|---|---|---|---|
| 2,844,964 | 7/1958 | Guibert | 73/863.81 |
| 3,566,865 | 6/1968 | Hay | 73/863.83 |
| 3,896,673 | 7/1975 | Audouze et al. | 73/864.34 |
| 4,056,981 | 11/1977 | Kalka et al. | 73/863.85 |
| 4,294,124 | 10/1981 | Kalwaitis | 73/863.85 |
| 4,307,620 | 12/1981 | Jiskoot | 73/863.83 |
| 4,413,533 | 11/1983 | Diesel | 73/863.31 |
| 4,674,343 | 6/1987 | Larson | 73/863.86 |
| 4,791,821 | 12/1988 | Spencer | 73/863.86 |
| 4,823,623 | 4/1989 | Carpenter et al. | 73/863.86 |
| 4,879,915 | 11/1989 | Spencer | 73/864.74 |
| 4,939,940 | 7/1990 | Tsukida | 73/864.74 |
| 4,986,138 | 1/1991 | Spencer | 73/863.86 |
| 5,003,830 | 4/1991 | Spencer | 73/863.83 |
| 5,029,485 | 7/1991 | Marr | 73/864.34 |
| 5,038,623 | 8/1991 | Zeh | 73/863.83 |
| 5,060,529 | 10/1991 | Bals et al. | 73/864.74 |
| 5,092,988 | 3/1992 | Womack, II et al. | 73/864.34 |
| 5,133,938 | 7/1992 | Glanville et al. | 73/863.85 |

FOREIGN PATENT DOCUMENTS

| | | | |
|---|---|---|---|
| 2343239 | 9/1977 | France | 73/863.83 |
| 0725235 | 9/1942 | Germany | 73/863.83 |
| 2918768 | 11/1980 | Germany | 73/863.83 |
| 0798529 | 1/1981 | U.S.S.R. | 73/863.85 |
| 0868429 | 9/1981 | U.S.S.R. | 73/863.83 |

Primary Examiner—Hezron E. Williams
Assistant Examiner—George M. Dombroske
Attorney, Agent, or Firm—Gunn & Kuffner

[57] ABSTRACT

Improvements are set forth in the present disclosure for the sample taking system. It normally uses a valve which can be switched between two operative positions one delivering a sample. The valve lock mechanism is incorporated. Additional safety is provided by means of a blocking valve added to the circuit. These control the delivery of sample through a twin needle system which is inserted through the septum of a sample receiving container. That container is formed of a non-round shape supported in a mounting fixture which assures that it does not rotate to thereby avoid tearing the septum with the needles. In addition, a purge gas flow route is defined through the system and is discharged to atmosphere. This discharge is through a cartridge filter having duplicate ends. The ends are closed by membranes to permit inert gas to flow there through. The bottom membrane is pervious while the top membrane is impervious, but it is punctured by a needle to introduce the sample. The membranes, housing and particulate filter material are all combustible in a furnace for destruction of the equipment.

13 Claims, 3 Drawing Sheets

SAMPLE SYSTEM

The present disclosure is a continuation in part of previously filed U.S. application Ser. No. 895,788, which was filed on Jun. 9, 1992, now U.S. Pat. No. 5,279,167, and also application Ser. No. 882,033, which was filed on Jul. 13, 1992, still pending.

BACKGROUND OF THE DISCLOSURE

The structures set forth in the foregoing applications are believed to be systems which are quite useful for obtaining samples. They set forth devices which obtain samples in many different circumstances. One of the above mentioned disclosures is directed to a liquid sample taking system. The other disclosure is directed to a permanently installed sample taking system. As will be understood, those two systems are complimentary in operation and benefit. More specifically, they set forth sample taking systems which capture a liquid sample which is placed in a sample container so that fugitive emissions to atmosphere do not occur. The sample, once obtained, is readily transferred to a laboratory for testing. This arrangement is believed to be effective for the convenient capture of a small quantity which enables laboratory testing from a variety of locations, all accomplished without fugitive emissions to atmosphere. The present disclosure however sets forth certain enhancements. These enhancements are particularly important with a view of obtaining regular test of the gas or liquid stream which is periodically tested.

Going now to the structure which is set forth in this disclosure, several aspects of the test equipment have been enhanced. One aspect is particularly important, namely, the safe and controlled mechanism by which the test equipment is switched off and on. In one aspect of the present disclosure, the test equipment is provided with a two position, six port valve. There is the always the possibility that the valve will be operated prior to attachment of the sample holding bottle. To avoid this, the present disclosure sets forth a mechanism by which the two way, six port valve is locked. The locking mechanism is particularly important so that the valve cannot be accidentally opened and deliver sample prior to attachment of the bottle. It is constructed with an interlock mechanism which prevents such opening. More specifically, it is constructed with an additional blocking valve. The incorporation of the valve just mentioned and the interlock mechanism assures that the valve is not operated until the system is ready to operate.

One aspect of the present system is the provision of an improved filter. The filter is intended to capture any trace components mixed with a nitrogen purge gas flow discharged to atmosphere. The filter cartridge is provided with two ends, the two ends being provided with protective caps, and the two ends are constructed with membranes across them. At one end, this permits a needle to be inserted through the protective membrane to introduce the gas flow. The flow into the filter escapes through the opposite end which is provided with a transverse pervious membrane. The two membranes prevent the filter material, normally activated charcoal, from escaping. Moreover, the cartridge shell as well as the two ends are constructed of materials which are readily consumed in a furnace. Likewise, the two membranes incorporated in the disposable filter are combustible. One important object of the present system is to provide a disposable purge gas filter which can be incinerated totally without creating dangerous residue. The sample bottle that is incorporated in the present system is normally installed by positioning the sample bottle on a pair of parallel needles. The two needles are constructed with points extending into a septum which is punctured by insertion of the needles. The septum isolates the interior of the sample container. The septum may be torn should the sample container be rotated after the two needles are inserted through the septum. The possibility of tearing creates a severe risk of atmospheric leakage. This can destroy the integrity of the measured sample. This is prevented in this embodiment. This enhances and improves the safety of operation and reduces the risk of leakage. Moreover, the sample bottle is totally protected from the time of installation through removal when transferred to the laboratory.

Other important aspects of the improvements set forth herein enable the two referenced systems in the above mentioned patent applications to be enhanced in operation in many aspects.

BRIEF DESCRIPTION OF THE DRAWINGS

So that the manner in which the above recited features, advantages and objects of the present invention are attained and can be understood in detail, more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

DETAILED DESCRIPTION OF THE PREFERRED EMBODIMENT

Figure 1:
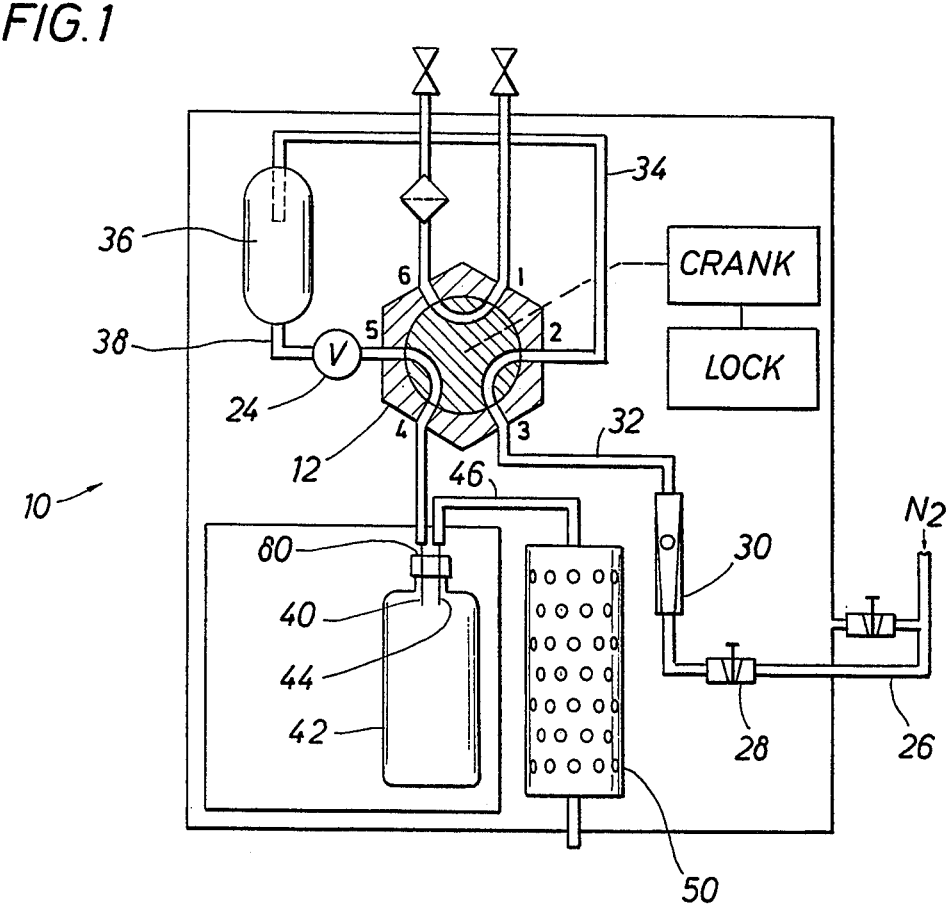
FIG. 1 is flow diagram of a sample taking system showing a sample containing bottle and filter which in this flow diagram are components requiring periodic installation and removal.
Figure 2:
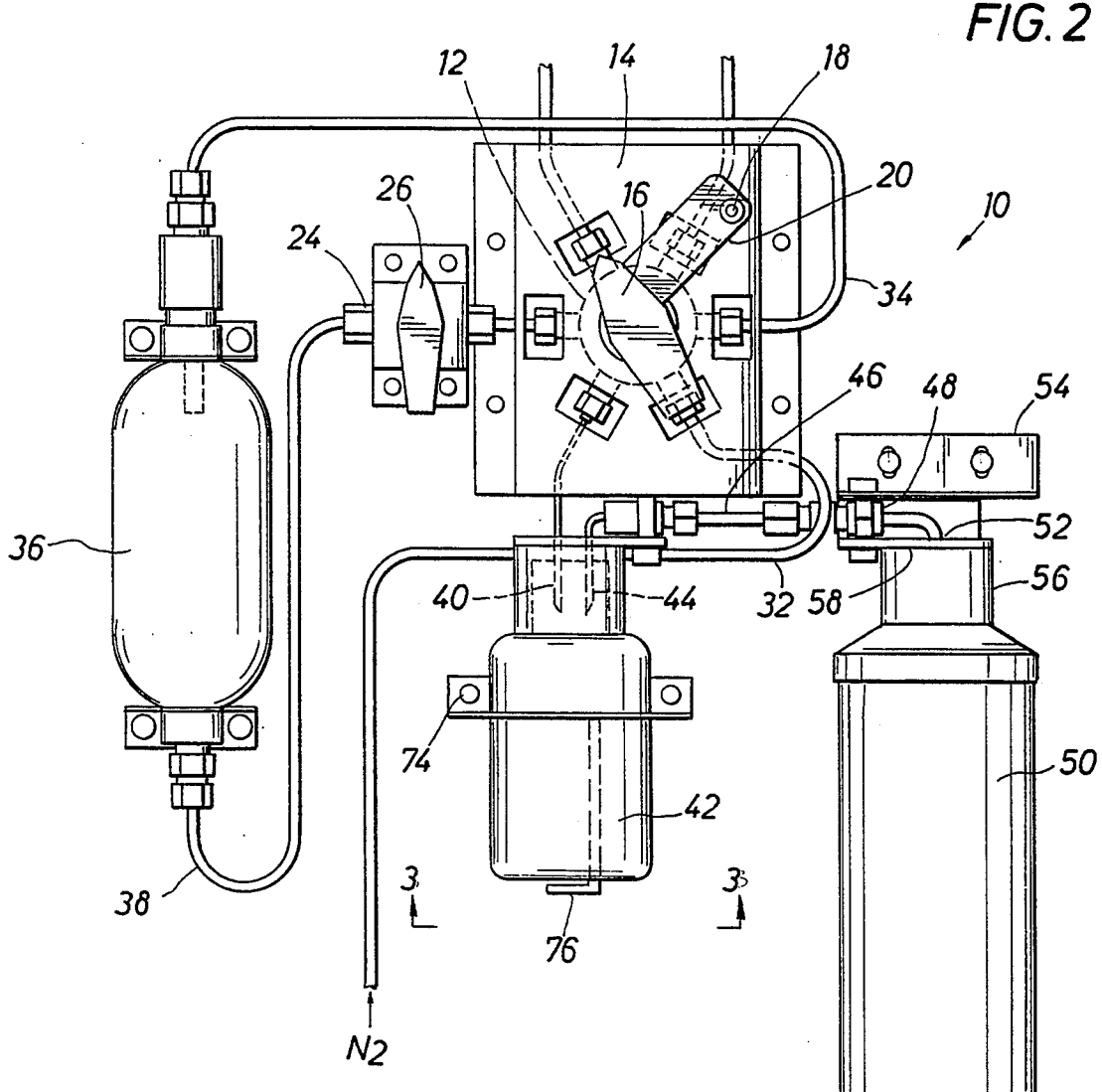
FIG. 2 is a mechanical assembly of a sample taking system which includes a sample containing bottle and which also includes a purge gas filter wherein the bottle and filter are periodically replaced, and also showing the control valve interlocks to prevent accidental delivery to atmosphere.

In the drawings, the numeral 10 identifies a flow system for installation with a process, this being shown in application Ser. No. 882,033 mentioned above. In this particular instance, the flow system involves delivery of a purge gas from a nitrogen source which is circulated through a two position, six port valve. In this particular embodiment, the valve is shown to have a crank which moves the valve between stops. There are two positions permitted by crank or hand control. There is also a lock which locks the valve in a particular position. As will be discussed with regard to FIG. 2 of the drawings, this is incorporated to assure that accidental operation does not occur whereby sample is delivered to atmosphere. In addition to that, there is a blocking valve incorporated as shown in FIG. 1, and these will be discussed in particular with regard to FIG. 2 of the drawings. Going to FIG. 2, the system is shown where the structural components are positioned in a cabinet or housing substantially as illustrated in FIG. 2 of the drawings. Here, the six port valve 12 is located on the backside of a support panel 14 which structurally supports that valve. The valve 12 is operated by the hand held crank 16 which is extended on the front of the panel 14. The crank 16 is rotatable between first and second positions. In one position, no test can be conducted. In another position a test is conducted. In the first position, a pathway is defined through the equipment so that the nitrogen purge gas is able to flow, thereby introducing the purge gas to the various lines to assure that the sample container is cleared.

Going first to this structure, the crank 16 is at one position as shown in FIG. 2 and rotates clockwise through an angle of 60° to the second position. It cannot be rotated as shown in FIG. 2 because it is blocked from rotation by a pivoted lock arm 20 which is mounted on a pivot 18. The lock arm 20 can be rotated out of the way by rotation in a clockwise direction. It is operative by gravity to move to the locking position illustrated. The significance of this feature will be noted in some detail below.

The mechanical layout of the equipment shown in FIG. 2 further includes a blocking ball valve 24. The valve 24 is connected in the system as will be described for blocking. It is a valve which moves to a fully closed position when the handle 26 points upwardly. It is rotated to a fully open position on rotation through 90°. In other words, when the handle 26 is horizontal, this valve is open. The significance of this valve will be understood below.

Returning now to FIG. 1 of the drawings, certain aspects of the lock 20 cooperative with the valve 12 and also the blocking valve 24 will be observed. In FIG. 1 of the drawings, the valve 12 is shown in schematic fashion where it connects with a number of lines. These lines will be described beginning with the introduction of the purged gas. The nitrogen input line 26 delivers nitrogen through a needle valve 28 which controls the flow volume. A meter 30 is included. This provides a visual indication of the flow rate of nitrogen. The nitrogen is introduced to the valve 12 through the flow line 32, this line being also shown in FIG. 2 of the drawings. It flows into the third port of the six port valve 12 and out through the flow line 34. The line 34 is also shown in FIG. 2. The flow is delivered to a sample tank or chamber 36. The tank or chamber 36 measures the sample size. In other words, it assures that a proper size of sample is delivered. The size of the tank 36 correlates to the size of the sample container as will be discussed. When the equipment is installed, the sample tank 36 is sized so that it matches the sample container that will be removed. The sample tank 36 has the form of a small pressurized tank. One size of tank will provide a sample dependent on the filling tube depth in the tank. If the tank 36 has a maximum size of 1000 ml, it can be adjusted in size to a smaller sample by cutting the length to control filling. In effect, a gas head is captured above the liquid above the end of the tube.

The flow line continues from the tank 36 through a line 38 shown in both views and that line is input to the blocking valve 24. Fluid then flows through a line input to the fifth port of the valve. Tracing now through the schematic flow diagram of FIG. 1, in the illustrated position, gas flow from the fifth port flows out of the valve 12 through its fourth port and to a needle 40 where it is introduced into a sample container 42. The sample container 42 is voided through a second needle 44. The needle 44 provides an output from the small container 42 and connects with a line 46 which extends to a fitting 48. The fitting (see FIG. 2) is located so that it is an alignment structure for a removable cartridge filter 50. The cartridge filter 50 is incorporated for the purpose of permitting the purge gas to flow to atmosphere after cleaning. The purge gas which is introduced into the disposable cartridge filter 50 flows out the bottom end of that structure as will be described. Moreover, the fitting 48 supports a bent needle 52 which has a point extending downwardly and which is located inside of the cartridge filter 50 (see FIG. 5).

Figure 4:
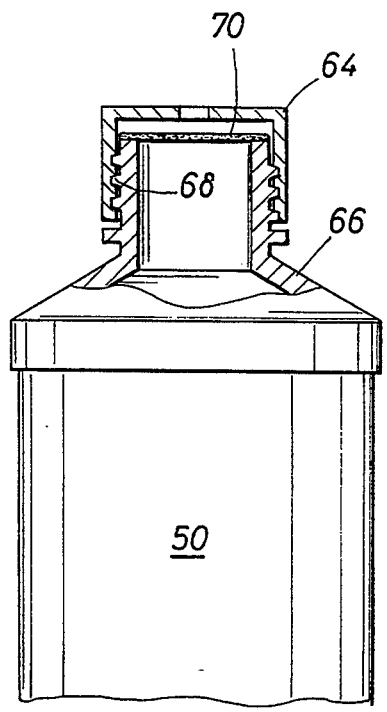
FIG. 4 is a view of the end of the purge gas filter with a cap over the end.

Continuing with the structure as illustrated in FIG. 2 of the drawings, the fitting 48 is supported on an L shaped bracket 54 which is mounted on the cabinet. More specifically, the fitting and bracket also support a downwardly extending circular collar 56 which encircles the upper end of the filter 50. As illustrated in detail in FIG. 2 of the drawings, the circular collar serves as an alignment mechanism. It is affixed to the bottom of a mounting plate 58 which is attached to the bracket 54 and which is cooperative with the needle and fitting 48. In like fashion, the very bottom end of the equipment has a duplicate collar 60 supported on an L shaped bracket 62 which is mounted on the panel. The collar 60 and the support bracket plate are both provided with perforations so that gas introduced into the cartridge 50 can escape to atmosphere. Going now to FIGS. 4 and 5 jointly, the cartridge 50 is shown in some additional detail. It is provided with a threaded cap 64 having a central hole in it. The upper end is constructed with a tapered, conic neck 66 which terminates in an upwardly extended threaded collar 68 which is closed over at the top end by a perforable membrane 70. As shown in FIG. 4, the membrane 70 is protected by the cap. At the time of installation, the neck of the cartridge 50 is positioned at the cylindrical ring 56, and the needle 52 is forced through the membrane 70. Ideally, the needle 52 is located at the center of the ring 56 so that rotation of the cartridge, even though unnecessary and unintended, does not tear the septum 70. The system 70 is thus perforated by the needle.

The lower end of the cartridge is constructed in the same fashion. Since the two ends are identical, realistically, either can be the inlet end and either can be the outlet end except for differences in the two membranes. The cartridge is packed with activated charcoal or other graphite type filter materials.

The shell and neck of the cartridge are made of available plastics such as polyethylene. The caps are preferably plastic or metal caps. The top end septum 70 can be a composite layer such as a backing of Teflon (a trademark of DuPont) with a resilient foam on the inside surface. The membrane for the opposite end is pervious to enable purge gas to flow through the filter and escape to atmosphere. The membrane can be woven fabric. The fabric membrane is pervious to enable gas escape while preventing particulate escape.

The cartridge 50 has a specified volume, perhaps in the range of 1 to 2 liters. It is packed with particulate charcoal which has a surface area in the range of about 50 to 300 square meters per gram. It has a surface retention ability which can hold any trace gases which are introduced with the nitrogen. The purged nitrogen flow normally percolates through the carbon material and flows from one end to the other of the cartridge and escapes to atmosphere.

Figure 3:
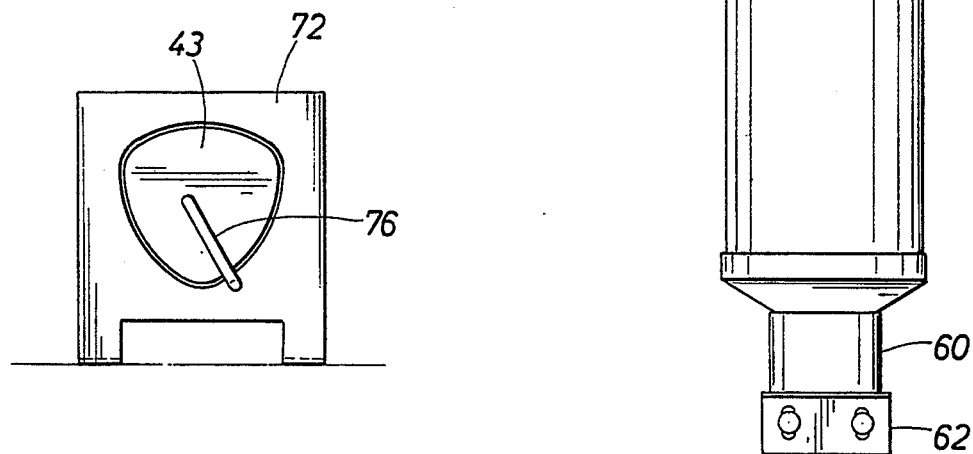
FIG. 3 is a view of the end of the sample container showing a support for the sample container and the profile of the sample container which prevents rotation which would otherwise result in tearing of the septum on the container.

Another important aspect of the present invention is the sample container 42. It is constructed of a shape which will not rotate. It is held in position by the mounting bracket 72 shown in FIG. 3 of the drawings. That bracket protrudes from the cabinet wall outwardly and is fastened to the cabinet by suitable bolts 74 shown in FIG. 2 of the drawings. The mounting bracket 72 supports a downwardly extending rod which has a bent lower end 76 which is readily rotated to a position where it is below the container 42. The container 42 is supported on this bent rod 76 in an upright position. In the upright position, it is able to rest on the rod 76. The weight is relatively light because it is normally used in capturing a small sample, typically one liter and preferably only a fraction of a liter. The container 42 is typically calibrated to a particular size such as 500 ml. Whatever the fact, it is a sealed supported in this fashion.

This is not a round container. This container shape, in conjunction with the bracket 72 which supports it, prevents rotation. Rotation may well destroy the integrity of the sample which is captured in the container 42. More specifically, the container 42 incorporates a diaphragm 80 illustrated in dotted line in FIG. 2 of the drawings. The diaphragm 80 is perforated by the needles 40 and 42. As shown previously in FIG. 1 of the drawings, the diaphragm 80 is a seal which prevents the interchange of atmosphere into the container. The diaphragm or septum is a barrier to interchange. When the sample container 42 is installed on the two needles 40 and 44, rotation of the container will tear the membrane 80. Rotation is therefore undesirable and to this end, the bracket 72 is constructed with an opening in it which prevents rotation. Thus, the rod 76 is rotated to the side, the container 42 is forced upwardly and positioned in the surrounding collar 82 shown in FIG. 2 of the drawings and the needles 40 and 42 are forced into the septum by perforation through the septum 80. After the bottle has been moved sufficiently above the rod 76, the rod 76 is then rotated back to the support position. The rod 76 then supports the container 42 indefinitely.

Going now to benefits of this system in operation, the following sequence should be noted. Assume that the cabinet shown in FIG. 1 in schematic form is installed and connected with a system to measure a liquid sample. One of the initial steps before installing the expendable components involves purging the lines. Nitrogen gas flow is introduced through the line 26, metered by the valve 28, and the pressure is adjusted so that the nitrogen flow regulator 30 indicates the flow. Nitrogen flows through the line 32, the valve 12, the line 34, and the calibrated tank 36. That is purged so that the only fluid remaining in it is nitrogen. That however requires opening of the valve 24 to permit flow out through the needle 40. This purges nitrogen through all of the lines just mentioned. A fresh sample container 42 is installed in the manner just described with regard to FIG. 3. Likewise, a disposable filter cartridge 50 is installed. A sample is then taken. At the time that a sample container is removed, the valve 24 is momentarily closed to prevent sample escape to atmosphere but the valve 24 is normally left open at other times. A flow of nitrogen into and out of the sample container 42 utilizes the needles 40 and 44. Nitrogen flows out through the cartridge 50. At this juncture, all of the lines have been purged and are substantially filled only with the purge gas. The valve 12 is operated. At the time of its operation, movement is blocked by the lock 20 shown in FIG. 2 of the drawings. The lever or lock 20 is rotated clockwise around the pivot 18. This frees the handle 16 to operate. It is operated to the alternate position. At this moment, however, no purge gas or liquid sample can flow into the sample container 42. It is also opened for flow. Sample is then delivered from the process to fill the tank 36. Surplus sample is recirculated back to the process. When that occurs, the sample container 42 is continually purged with nitrogen gas because operation of the valve 12 directly connects the fourth port to the third port of the valve thereby directing the purge nitrogen gas into sample container.

The valve is restored to the original position; that position is illustrated by the connection of the lines through the valve 12 as shown in FIG. 1. The purge nitrogen gas is forced through the tank 36 and delivers the tank ingredients under pressure into the sample container. Assume for purposes of illustration that the whole tank holds 500 ml of the sample; the filling tube reduces the volume to match the sample container which is sized to hold a smaller portion. The sample is delivered into the sample container 42. The recirculation liquid, assumed here for purposes of illustration, is sent back to the process. The tank and its filler tube store only the required amount. This assures the correct amount for the container, an amount tailored to container capacity.

Figure 5:
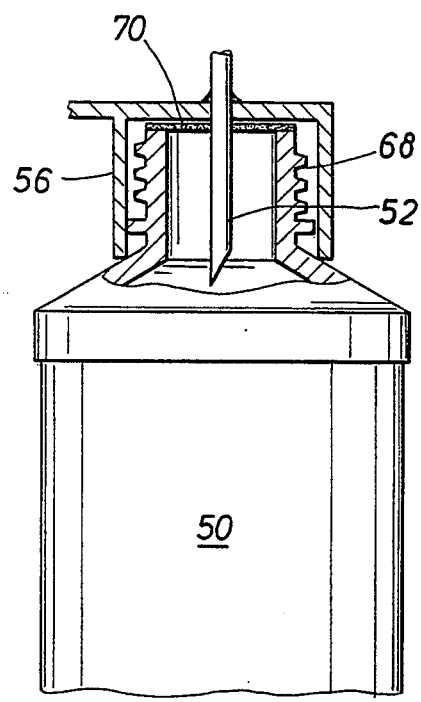
FIG. 5 is a view similar to FIG. 4 showing the filter installed for use.

Perhaps many sample containers 42 will be filled over a few days. Over the period of time, the cartridge 50 will become depleted by absorbing all that can be absorbed into the filtration material. Ultimately, it is necessary to replace the cartridge 50. Replacement is accomplished by removing the cartridge 50 from the mounting mechanism which is illustrated in some detail in FIG. 2. This can be done simply by dismounting the bracket 62 at the lower end and dropping the cartridge filter downwardly. Conveniently, the bracket 62 is mounted by bolts and it is therefore readily removed. Once removed, the fresh cartridge replaces the spent or used cartridge. The interior of the used cartridge is sealed to prevent particulate material escape. It can then be taken at a convenient time to a point of disposition. There, it can be incinerated, and all the components of the cartridge are consumed, including the shell, the heads, the membranes and the contents. Obviously, when the used cartridge is removed, a new one is installed. The new one is installed after removing the old cartridge and stabbing the new cartridge upwardly so that the needle 52 penetrates the membrane 70 as shown in FIG. 5. Then, the cartridge is locked in place by repositioning the bottom bracket 62. This secures the cartridge 50 until its replacement is required at another time. All the while, the system can be either operated to take samples on a regular basis, perhaps filling 50 or 100 sample containers over a period of several days or several weeks. Moreover, the sample containers 42 are installed and removed in the fashion previously described.

Figure 6:
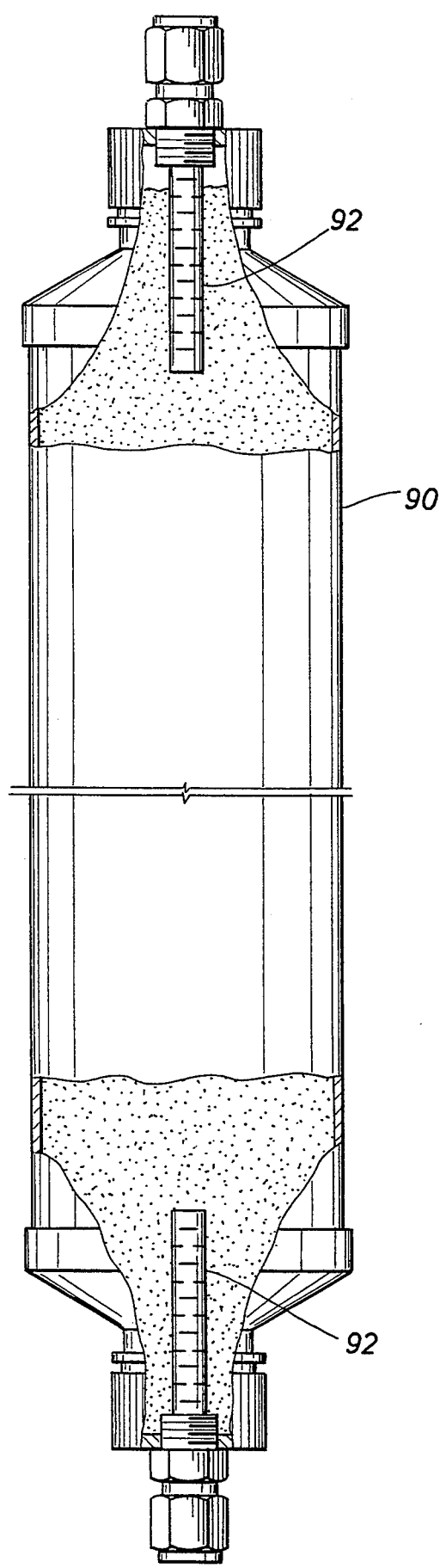
FIG. 6 is an alternate filter construction.

FIG. 6 shows a cartridge 90. The ends of the cartridge have fittings for tubing connection; and there are also tubings positioned in the cartridge. The tubing is cut with multiple slots to enable passage through the tubing into the cartridge. The tubing 92 ends in a crimped, narrow tip. The tubing is held in the cartridge by well known tubing fittings. Thus, the ends of the cartridge 90 include the necessary fittings and enable connection into a system.

While the foregoing is directed to the preferred embodiment, the scope thereof is determined by the claims which follow:

I claim:

1. A sample collection system for obtaining a sample from a process wherein the sample system comprises:
   (a) a valve means controlling delivery of the sample;
   (b) a demountable sample receiving container;
   (c) conduits connected to deliver from said valve means a sample into said sample container;
   (d) means for locking said valve means so that said sample system is not operative to deliver sample in the absence of the sample receiving container;
   (e) a non-rotational sample container; and
   (f) an exit gas filter means wherein
   (g) said sample container is shaped so as to prevent rotation about its vertical axis.

2. The system of claim 1 wherein said valve means comprises a serially connected valve which is switched between flow and no flow positions for the flow of the sample.

3. The apparatus of claim 1 wherein said lock means comprises a handle exposed for operator use and is connected with said valve means and further including a moveable latch blocking said handle and thereby preventing rotation.

4. The apparatus of claim 1 wherein the exit gas filter means is filter cartridge comprising an elongate housing enclosing a particulate filter material, and having spaced ,ends wherein each end incorporates an opening and said openings are covered by transverse closure members, one of said transverse members permitting inert gases to flow through said one transverse member and the other of said members including a needle penetrated septum and further wherein said filter housing and membranes define an integral structure.

5. The cartridge of claim 4 wherein said cartridge is formed of readily disposed materials by furnace destruction.

6. The cartridge of claim 4 wherein said cartridge is filled with a carbon filtrate material.

7. A sample container and cooperative support with a sample collection system wherein said container support aligns said sample container for movement into an operative and connected position without rotation and further wherein said container and support interlock to prevent rotation, wherein said container fits within a mating and conforming triangular opening in said support bracket for preventing rotation of said container while in use.

8. The apparatus of claim 7 further including a triangular opening in said support aligned with and supporting said container which is constructed with a mating and locking triangular shape.

9. The apparatus of claim 8 including an extending neck on said sample container closed by a transverse septum preventing leakage from the container to the exterior and wherein said container septum is adapted to be perforated by a pointed needle for delivery of a sample into said container.

10. A sample container for use with a sample collection system which removes a small sample for subsequent testing and the system includes valve means for controlling delivery of the sample comprising:
   (a) a sample receiving container and cooperative container support wherein said container support aligns said sample receiving container for movement into an operative and connected position without rotation and further wherein said container is locked to prevent rotation during use;
   (b) an extending neck on said container closed by a transverse septum preventing leakage from the container to the exterior and wherein said container septum is adapted to be perforated by a pointed needle for delivery of a sample into said container;
   (c) a needle support aligning said needle for container filling and providing a sample flow said valve means to said needle; and
   (d) a purge waste line connected from said needle and container to enable said container to vent surplus sample for disposal, wherein
   (e) said container is shaped so as to prevent rotation about its vertical axis.

11. The apparatus of claim 10 wherein said sample container is approximately triangular in cross sectional shape.

12. The apparatus of claim 11 wherein said triangular container fits within a mating and conforming triangular opening in a support bracket for aligning said container.

13. The apparatus of claim 12 wherein said container and said support bracket enable cooperation solely with linear motion.

* * * * *